(12) United States Patent
Patel et al.

(10) Patent No.: US 7,692,047 B2
(45) Date of Patent: Apr. 6, 2010

(54) PROCESS FOR THE ALKYLATION OF PHENOLS

(75) Inventors: Anjali Uday Patel, Vadodara (IN); Nikunj Bhagwatiprasad Bhatt, Vadodara (IN)

(73) Assignee: Secretary, Department of Science & Technology, New Delhi (IN)

( * ) Notice: Subject to any disclaimer, the term of this patent is extended or adjusted under 35 U.S.C. 154(b) by 0 days.

(21) Appl. No.: 11/861,763

(22) Filed: Sep. 26, 2007

(65) Prior Publication Data

US 2008/0114192 A1 May 15, 2008

(30) Foreign Application Priority Data

Sep. 26, 2006 (IN) ......................... 2113/DEL/2006

(51) Int. Cl.
*C07C 37/14* (2006.01)
(52) U.S. Cl. ........................ 568/785; 568/786; 568/787; 568/789
(58) Field of Classification Search ................. 568/785, 568/786, 787, 789
See application file for complete search history.

(56) References Cited

U.S. PATENT DOCUMENTS

| | | | |
|---|---|---|---|
| 4,267,394 A | | 5/1981 | Parlman |
| 4,323,713 A | * | 4/1982 | Engel .......................... 568/766 |
| 4,532,368 A | | 7/1985 | Swanson et al. |
| 5,300,703 A | | 4/1994 | Knifton |
| 5,399,786 A | | 3/1995 | Queiroz et al. |
| 5,475,178 A | | 12/1995 | Del Rossi et al. |
| 5,866,739 A | * | 2/1999 | Soled et al. .................. 585/467 |
| 6,204,424 B1 | | 3/2001 | Yadav et al. |

FOREIGN PATENT DOCUMENTS

| | | |
|---|---|---|
| JP | 61-200934 | 9/1986 |
| JP | 61-251633 | 11/1986 |

OTHER PUBLICATIONS

Badamali et al., "Tertiary butylation of phenol over mesoporous H-FeMCM-41." *Catalysis Letters* 65(2000): 153-157.
Sakthivel et al., "Vapour phase tertiary butylation of phenol over sulfated zirconia catalyst." *Catalysis Letters* 72: 3-4(2001): 225-228.
Sakthivel et al., "para-Selective t-butylation of phenol over mesoporous H-A1MCM-41." *Microporous and Mesoporous Materials* 39(2000): 457-463.
Anand et al., "Tertiary butylation of phenol over HY and dealuminated HY zeolites." *Journal of Molecular Catalysis A: Chemical* 193(2003): 251-257.
Dumitriu et al., "Effects of channel structures and acid properties of large-pore zeolites in the liquid-phase tert-butylation of phenol." *Journal of Catalysis* 218(2003): 249-257.
Shen et al., "Comparative studies on alkylation of phenol with tert-butyl alcohol in the presence of liquid or solid acid catalysts in ionic liquids." *Journal of Molecular Catalysis A: Chemical* 212(2004): 301-308.
Kozhenvnikov, "Friedel-Crafts acylation and related reactions catalysed by heteropoly acids." *Applied Catalysis A: General* 256(2003): 3-18.
Shinde et al., "tert-Butylation of phenols using tert-butyl alcohol in the presenece of FeCl3-modified montmorillonite K10." *Applied Catalysis A: General* 276(2004): 5-8.
Zhang et al., "Alkylation of phenol with tert-butyl alcohol catalysed by zeolite Hβ." *Applied Catalysis A: General* 166(1998): 89-95.
Zhang et al., "Alkylation of phenol with tert-butyl alcohol catalyzed by large pore zeolites." *Applied Catalysis A: General* 207(2001): 183-190.

* cited by examiner

*Primary Examiner*—Elvis O Price
(74) *Attorney, Agent, or Firm*—Merchant & Gould P.C.

(57) ABSTRACT

The present invention relates to an improved process for the selective alkylation of phenols using heteropolyacid catalyst supported onto zirconia under mild conditions. The process is economically viable since the catalyst regenerated after the initial reaction on further use gives the product in high yield.

11 Claims, No Drawings

PROCESS FOR THE ALKYLATION OF PHENOLS

FIELD OF INVENTION

The present invention relates to an improved process for the selective alkylation of phenols. The present invention in particular relates to an improved process for selective phenol alkylation with catalyst regeneration.

BACKGROUND OF INVENTION

It is known in the art that the alkylation of phenol is an industrially important reaction. The products obtained are either used directly or as chemical intermediates for bulk industries like petrochemicals, fine chemicals, agrochemical etc. The reaction is usually carried out by using liquid Friedel-Crafts catalysts such as $AlCl_3$, $BF_3$, $FeCl_3$ and $ZnCl_2$. The same reaction can also be carried out by making use of a number of catalysts under different conditions and using different alkylating agent in order to get ortho and para alkylphenols.

U.S. Pat. No. 4,267,394 discloses a process involving a reaction of phenol with iso-propanol in the presence of diethyl ether complex of BF3 in phosphoric acid diluent at a temperature range of 70° C. to 90° C. to produce the ortho-isomer.

U.S. Pat. No. 4,532,368 discloses a process for the production of meta and para-alkylphenols from phenol and olefins in the presence of silicalites and ZSM-5 as catalyst at a temperature of 200° C. to 500° C.

U.S. Pat. No. 5,399,786 discloses a process for the preparation tert butyl-p-phenol by the reaction of phenol with alkyl tert-butyl ether in the presence of a protonated strong acid type catalyst in the temperature range of 60° C. to 130° C. and pressure ranging between atmospheric pressure to 5 kg/cm.sup.2.

U.S. Pat. No. 5,475,178 discloses a process for the alkylation of phenol with olefins using phosphotungsticacid supported on MCM-41 at a temperature range of 0° C. to 500° C. degree C. and at a pressure ranging from 0.2 to 250 atmosphere. In the prior art, stress is given to the preparation of the catalyst. MCM-41 is used as a support. For alkylation reaction, olefin is used as an alkylating agent and the reaction is carried out under pressure. Further the process does not claim regeneration of the catalyst. In the present invention, hydrous zirconia is used as a support. The present invention describes the alkylation of phenol with alcohol under atmospheric pressure. Also the present invention describes a simple process for the regeneration of the catalyst. The increased yield, selectivity and catalyst regeneration in the present invention is attributed to the novel reaction conditions, alkylating agent as well as nature of the catalyst support.

U.S. Pat. No. 5,300,703 discloses a process for the selective synthesis of p-nonyl phenol by reacting phenol with olefins in the presence of catalysts selected from the group of 12-tungstophosphoric acid, 12-tungstosilicic acid, 12-molybdosilicic acid supported on an inert oxide such as titanium dioxide, aluminium oxide and silicon oxide. The reaction is carried out at 90° C. under pressure of 100 psi. The maximum % conversion is 91 and the para-nonyl phenol to ortho-nonyl phenol weight ratio is 10.

U.S. Pat. No. 6,204,424 discloses a process for the alkylation of phenol with tertiary-butyl ether and benzyl chloride in the presence of solid acid catalysts such as sulphated oxides of different metals such as Zr, Ti, Fe, Al, Sn and Bi. The catalysts are also reused.

Japanese patents 61251633 and 61200934 disclose the production of highly pure para-tertiary-butylphenol by the reaction of phenol with isobutylene and butene in the presence of activated clay at 10-120° C. and production of the same mentioned product by the reaction of phenol with butene in the presence of aluminium phenoxide and a nitrogen containing base at 30-200° C. respectively.

The prior art processes do not have the advantage of 100% conversion with respect to reaction yield. The present invention has its surprising effect in 100% conversion with respect to reaction yield and 97.2% selectivity with respect to p-tert butylphenol formation.

A number of research papers have been published on the synthesis of alkyl phenol in vapour phase. Selvam and co workers (Catal. Lett. 65, 153, 2000) have reported vapour phase reaction of phenol with tert-butyl alcohol using Fe—MCM-41 at 175° C. They have found 87% selectivity for p-tert-butyl phenol with 21.1% conversion. The same reaction was carried out in presence of sulphated Zirconia (Catal. Lett. 72, 3, 2001) and Al—MCM-41 (Micro. Meso. Mater. 39, 457, 2000) at the same temperature by the same authors. Sulphated Zirconia and Al—MCM-41 gave 57.8% and 35.9% conversion and 86.5 and 83.4% selectivity for p-tert-butyl phenol respectively.

HY and Hβ were used for the vapour phase reaction of phenol with tert-butyl alcohol at 105° C. and 145° C. respectively by Zhang and Co workers (Appl. Catal. A. 207, 183, 2001; 166, 89, 1998). They have reported 90.4% and 76.3% selectivity for p-tert-butyl phenol with 46.2% and 95.8% conversion for HY and Hβ respectively.

Anand and co workers (J. Mol. Catal. A. 193, 251, 2003) have reported 62.6% selectivity for p-tert-butyl phenol with 45.5% conversion by the vapour phase reaction of phenol with tert-butyl alcohol using Zeolites HY at 170° C.

A number of procedures have also been reported under liquid phase. Samant and co-workers have reported (Appl. Catal. A 276, 5, 2004) liquid phase tert-butylation of phenol in presence of k-10 clay and FeCl3/k-10 clay. The process gives 100% conversion with 62.0% and 66.8% selectivity for p-tert-butylphenol respectively.

V. Hules reported( J. Catal, 218, 249, 2003,) 52.7% conversion with 23.0% selectivity for p-tert-butylphenol using USY catalyst, 54.2% conversion with 80.3% selectivity for p-tert-butylphenol using Zeolite-β, 28.8% conversion with 49.1% selectivity for p-tert-butylphenol using Mordenite, 12.6% conversion with 79.5% selectivity for p-tert-butylphenol using HZSM-5, and 31.5% conversion with 99.3% selectivity for p-tert-butylphenol using H-β as the solid acid catalyst in presence of ionic liquids such as [bmim]PF6, [omim]BF4 and [hmim]BF4.

Y. Shen and co-workers have reported (J. Mol. Catal. A 212, 301, 2004) 44.8% conversion with 49.0% selectivity for p-tert-butylphenol with tungstophosphoricacid supported onto MCM-41 as catalyst.

Of all the reactions described in the art, there is no reaction reported with more than 80% selectivity for p-tert-butylphenol in liquid phase under mild conditions. Although the heteropolyacids are active for alkylation reaction, it is known that deactivation during these reactions is significant.

Especially in alkylation reactions, the catalysts get deactivated due to the coke formation. Traditionally removal of coke from the catalysts was carried out by heating the catalyst at 500° C. The traditional method cannot be applied to the heteropolyacids as they decompose at that temperature.

The present invention describes a novel catalyst regeneration method. The present inventors have for the first time developed a method for regenerating the heteropolyacid by heating at 300° C.

It is known in art that Kozhevnikov has reported (Appl, Catal. A: General 256, 3, 2003) that the recycling of heteropolyacid catalysts is the key issue to their applications. Subsequent regeneration of the same is quite difficult.

The present inventors have surprisingly found that heteropolyacid catalysts can be regenerated and also reused for the same alkylation reaction. The present invention affords a process which is very high yielding and also economically viable as the catalyst can be reused after a simple workup.

OBJECT OF THE INVENTION

It is an object of the present invention to provide a high yielding and selective process for the tert-butylation of phenol in liquid phase.

It is a further object of the present invention to provide a process for the tert-butylation of phenol in liquid phase with catalyst regeneration.

It is yet another object of the invention to provide a process for the tert-butylation of phenol in liquid phase with comparable selectivity in liquid phase by the use of regenerated catalyst.

SUMMARY OF THE INVENTION

According to an aspect of the present invention there is provided an improved process for the selective alkylation of phenols or substituted phenolic compounds comprising the steps of:
 i. Mixing alkylating agent and phenol in appropriate mole ratio;
 ii. Addition of heteropolyacid catalyst of specific loading;
 iii. Heating at around 50° C.-90° C. for 1 to 10 hours.

According to another aspect of the present invention there is provided a process for the regeneration of heteropolyacid catalyst from the alkylation reaction mass comprising the steps of:
 i. Separation of the catalyst from the final reaction mixture;
 ii. Washing the catalyst with double distilled water;
 iii. Drying at 100° C.;
 iv. Activation at 300° C.

DETAILED DESCRIPTION OF THE INVENTION

Alkylation of phenol is an industrially important reaction. The present invention provides an improved process for the tert-butylation of phenol in liquid phase under mild (80° C., atmospheric pressure) conditions with 100% conversion and around 95-97% selectivity for p-tert-butylphenol in the presence of fresh heteropolyacid catalyst. The advantage of the process lies in the simple regeneration of the catalyst. The regenerated catalysts give comparable selectivity for p-tert-butylphenol. The present invention is therefore economically viable.

The alkylation reaction is carried out in a 50 ml glass batch reactor provided with a double walled air condenser, magnetic stirrer and a guard tube. Alcohol to phenol is taken in a ratio ranging from 0.1:1.0 to 0.6:1.0 and catalyst is added in the amount (1.5%-7.5%). The resultant mixture is heated in the temperature range of 50° C. to 90° C. on magnetic stirrer for 1 h to 10 h.

According to an embodiment of the present invention the alkylation of phenol is carried out in a 50 ml round bottom flask provided with a double walled air condenser, magnetic stirrer and a guard tube. The ratio of alkylating agent (tert-butyl alcohol) to phenol is 1:10 and the heteropolyacid catalyst is added in the required amount. The resultant mixture is heated at 80° C. on a magnetic stirrer for 1 hour. The same reaction was carried out by varying alkylating agent to phenol mole ratio, amount of the catalyst, reaction time and temperature, and also with different % of loading of heteropolyacid onto zirconia agent as well as cresols.

For alkylation of phenol with tert-butyl alcohol, the obtained products o-t-BP, p-t-BP and o, p-di-t-BP were identified on gas chromatograph (Nucon 5700) using SE-30 column while m-t-BP was identified by AT-1000 column, and product identification was done by comparison with authentic samples as well as by a combined gas chromatography-mass spectrometry. Further, the isomers were separated by HPLC (Shimadzu) using Nucleosil $C_{18}$ column and identified by $^1$H NMR.

For alkylation of cresols with tert-butyl alcohol and alkylation of phenol with other alkylating agents, the reaction products were analyzed using SE-30 column, and product identification was done by a combined gas chromatography-mass spectrometry.

The heteropolyacid catalysts in the present invention are selected from Keggin type, namely 12-tungstosilicic acid, 12-tungstophosphoric acid supported on zirconia.

According to a most preferred embodiment of the present invention; the reaction conditions employed are catalyst loading 30% tungstophosphoric acid onto zirconia, amount of the catalyst 2.5% (amount of active species is 0.625%), mole ratio of phenol to alcohol 10:1, reaction temperature 80° C. and reaction time 6 hours.

According to yet another embodiment of the present invention; the heteropolyacid catalyst employed is 30% 12-tungstosilicic acid onto zirconia.

It gives 100% conversion with 95% selectivity for p-tert-butylphenol.

EXAMPLES

Example 1

Preparation of Keggin Type Heteropolyacid Catalysts (TPA/$ZrO_2$ and TSA/$ZrO_2$)

12-Tungstophosphoricacid and 12-tungstosilicic acid were supported on hydrous zirconia by impregnation method.

1 g of $ZrO_2$ was impregnated with an aqueous solution of $H_3PW_{12}O_{40}$ (TPA) (0.1 g/10 ml of conductivity water) or $H_4SiW_{12}O_{40}$ (TSA) at 100° C. with stirring for 10 hours. Material thus obtained was designated either as 10% TPA/$ZrO_2$ or as 10% TSA/$ZrO_2$. Same process was followed for the synthesis of a series of supported heteropolyacids containing 20-40% tungstophosphoricacid (0.2-0.4 gm/20-40 ml of conductivity water) or 20-40% tungstosilicic acid. The obtained materials were designated as 20% TPA/$ZrO_2$, 30% TPA/$ZrO_2$ and 40% TPA/$ZrO_2$ or as 20% TSA/$ZrO_2$, 30% TSA/$ZrO_2$ and 40% TSA/$ZrO_2$ respectively.

Example 2

Phenol Reaction Process

The alkylation reaction was carried out in a 50 ml glass batch reactor provided with a double walled air condenser, magnetic stirrer and a guard tube. Phenol (10.0 ml), tert-butyl alcohol (0.95 ml, mole ratio of 10:1.0), catalyst (0.25 gm, amount of active species is 0.0625 gm) were charged in the reactor. The resultant mixture was heated at 80° C. for 6 hours. After the completion of the reaction, no tert-butyl alcohol was found (confirmed by GC), the remaining phenol was distilled out and reused. The resultant products were identified by GC, GC-MS and HPLC.

Example 3

Cresol Reaction Process

The alkylation reaction was carried out in a 50 ml glass batch reactor provided with a double walled air condenser, magnetic stirrer and a guard tube. o-cresol (10.0 ml), m-cresol (10.5 ml) and p-cresol (10.5 ml), tert-butyl alcohol (0.95 ml mole ratio of 10:1.0), catalyst(0.25 gm, amount of active species is 0.0625 gm) were charged to the reactor. The resultant mixture was heated at 80° C. for 6 hours. After the completion of the reaction, no tert-butyl alcohol was found (confirmed by GC), the remaining cresol was distilled out and reused. The resultant products were identified by GC, GC-MS and HPLC.

Example 4

Regeneration of the Catalyst

The 1$^{st}$ recycling (R1) was carried out after separating it from reaction mixture only by filtration, washing with conductivity water (double distilled water), drying at 100° C. and treating in the temperature range of 200-400° C. The 2$^{nd}$ recycling (R2) was carried out by separating R1 from reaction mixture only by filtration, washing with conductivity water and drying at 100° C.

Example 5

Regeneration of Catalyst at Different Temperatures.

The above parameter was studied based on the following conditions:
 i. % conversion based on tert-butyl alcohol,
 ii. Catalyst used 30% TPA/ZrO$_2$ and 30% TSA/ZrO$_2$,
 iii. Mole ratio of alcohol to phenol 1:10,
 iv. Temperature 80° C.,
 V. Amount of the catalyst 0.25 g.

| Catalyst | % conversion of product formation | % selectivity o-t-BP | p-t-BP |
|---|---|---|---|
| R-TPA/ZrO$_2$ (200° C.)* | 53.0 | 6.2 | 93.8 |
| R-TPA/ZrO$_2$ (300° C.)* | 88.5 | 3.0 | 97.0 |
| R-TSA/ZrO$_2$ (300° C.)* | 76.0 | 24.8 | 75.2 |
| R-TPA/ZrO$_2$ (400° C.)* | 68.7 | 4.4 | 95.6 |
| R-TPA/ZrO$_2$ (500° C.)* | 34.2 | 3.7 | 96.3 |

*The number in parentheses indicates temperature at which regeneration has been carried out.

Example 6

Effect of Different Amount of the Catalyst and Different Mole Ratio of Tert-Butyl Alcohol to Phenol on Alkylation of Phenol.

The above parameter was studied based on the following conditions:
 i. % conversion based on tert-butyl alcohol,
 ii. catalyst used 30% TPA/ZrO$_2$/30% TSA/ZrO$_2$,
 iii. Reaction time 6 h,
 iv. Temperature is 80° C.

| Amount of the catalyst (g) | Mole ratio | % conversion | % selectivity o-t-BP | p-t-BP |
|---|---|---|---|---|
| 0.25 | 1:10 | 100/100 | 2.8/5.0 | 97.2/95.0 |
|  | 3:10 | 58.0/36 | 3.0/7.0 | 97.0/93.0 |
|  | 6:10 | 19.0/13.0 | 4.0/10.0 | 96.0/90.0 |
| 0.5 | 1:10 | 100/100 | 2.0/7.0 | 98.0/93.0 |
|  | 3:10 | 64.0/42.0 | 3.0/9.0 | 97.0/91.0 |
|  | 6:10 | 19.0/15.0 | 3.5/12.0 | 96.5/88.0 |
| 0.75 | 1:10 | 100/100 | 2.0/4.5 | 98.0/95.5 |
|  | 3:10 | 76.5/56.0 | 2.5/7.0 | 97.5/93.0 |
|  | 6:10 | 21.0/15.0 | 4.0/6.0 | 96.0/94.0 |

Example 7

Effect of Reaction Time on Alkylation of Phenol.

The above parameter was studied based on the following conditions:
 i. % conversion based on tert-butyl alcohol,
 ii. catalyst used 30% TPA/ZrO$_2$/30% TSA/ZrO$_2$,
 iii. Mole ratio of alcohol to phenol 1:10,
 iv. Temperature 80° C.,
 v. Amount of the catalyst 0.25 g.

| Reaction time in h | % conversion | % selectivity o-t-BP | p-t-BP |
|---|---|---|---|
| 1 | 90.0/90.0 | 3.0/6.0 | 97.0/94.0 |
| 3 | 96.0/95.0 | 3.0/7.0 | 97.0/93.0 |
| 4 | 96.7/97.0 | 3.5/5.0 | 96.5/95.0 |
| 5 | 98.5/98.0 | 3.2/4.5 | 96.8/95.5 |
| 6 | 100/100 | 2.8/5.0 | 97.2/95.0 |
| 10 | 100/100 | 3.0/5.0 | 97.0/(389)$^a$ |

Example 8

(a) % conversion and % selectivity for tert-butylation of cresols over 30% TPA/ZrO$_2$.
(b) % conversion and % selectivity for tert-butylation of cresols over 30% TSA/ZrO$_2$.

The above parameter was studied based on the following conditions:
 i. % conversion based on tert-butyl alcohol,
 ii. amount of catalyst 0.25 g,
 iii. mole ratio of phenol/cresol to tert-butyl alcohol 10:1,
 iv. Temp: 80° C.,
 v. Time: 6 hr.

(a)

| Substrate | Conversion (%) | Selectivity (%) o-isomer | p-isomer | TON |
|---|---|---|---|---|
| o-Cresol | 95.0 (82)$^a$ | 19.2 (—)$^a$ | 81.8 (100)$^a$ | 445 (384)$^a$ |
| m-Cresol | 95.0 (77.4)$^a$ | 100 (100)$^a$ | — (—)$^a$ | 445 (362)$^a$ |
| p-Cresol | 97.0 (83)$^a$ | 100 (100)$^a$ | — (—)$^a$ | 454 (389)$^a$ |

-continued

| Substrate | Conversion (%) | Selectivity (%) | | TON |
|---|---|---|---|---|
| | | o-isomer | p-isomer | |

[a]The number in parentheses indicate the result under homogeneous condition.

(b)

| | | Selectivity (%) | | |
|---|---|---|---|---|
| Substrate | % Conversion | o-isomer | p-isomer | TON |
| o-cresol | 87.5 (82)[a] | 20.3 (—)[a] | 79.7 (100)[a] | 412 (384)[a] |
| m-cresol | 97.0 (77.4)[a] | 100 (100)[a] | — (—)[a] | 456 (362)[a] |
| p-cresol | 93.8 (83)[a] | 100 (100)[a] | — (—)[a] | 441 (389)[a] |

[a]The number in parentheses indicate the result under homogeneous condition.

Example 9

Effect of Different % Loading of 12-Tungstophosphoricacid (TPA and TSA) on Alkylation of Phenol.

The above parameter was studied based on the following conditions:
i. % conversion based on tert-butyl alcohol,
ii. Amount of catalyst used 0.25 g,
iii. Mole ratio of alcohol to phenol 1:10,
iv. Reaction time 6 h,
v. Temperature 80° C.

| Catalyst | % conversion | % selectivity | |
|---|---|---|---|
| | | o-t-BP | p-t-BP |
| 20% TPA/ZrO$_2$ | 83.4 | 19.0 | 81.0 |
| 20% TSA/ZrO$_2$ | 71.0 | 23.0 | 77.0 |
| 30% TPA/ZrO$_2$ | 100 | 2.8 | 97.2 |
| 30% TSA/ZrO$_2$ | 100 | 5.0 | 95.0 |
| 40% TPA/ZrO$_2$ | 99.2 | 3.3 | 96.7 |
| 40% TSA/ZrO$_2$ | 78.0 | 5.0 | 95.0 |

We claim:

1. An improved process for the selective alkylation of phenols or substituted phenolic compounds comprising the steps of:
   i. Mixing an alkylating agent and a phenol substrate in a mole ratio of about 1:10 to about 6:10;
   ii. Adding a heteropolyacid catalyst, wherein the heteropolyacid catalyst has 20 to 40% loading; and
   iii. Heating for 1 to 10 hours at a temperature between 50° C.-90° C., wherein the alkylation is 95-97% selective for p-tert-butylphenol and 100% conversion is achieved.

2. The process for the selective alkylation of phenols or substituted phenolic compounds of claim 1, wherein the alkylating agent is tertiary butyl alcohol.

3. The process for the selective alkylation of phenols or substituted phenolic compounds of claim 2, wherein the tertiary butyl alcohol to phenol mole ratio is 1:10.

4. The process for the selective alkylation of phenols or substituted phenolic compounds of claim 1, wherein the heteropolyacid catalyst is of Keggin type.

5. The process for the selective alkylation of phenols or substituted phenolic compounds of claim 1, wherein the heteropolyacid catalyst is selected from 12-tungstophosphoric acid and 12-tungstosilicic acid.

6. The process for the selective alkylation of phenols or substituted phenolic compounds of claim 1, wherein the heteropolyacid catalyst is a fresh or a regenerated catalyst.

7. The process for the selective alkylation of phenols or substituted phenolic compounds of claim 3, wherein the heteropolyacid catalyst is present in the amount of 1.5%-7.5%.

8. The process for the selective alkylation of phenols or substituted phenolic compounds of claim 3, wherein the amount of the heteropolyacid catalyst is 2.5% (amount of active species is 0.625%).

9. The process for the selective alkylation of phenols or substituted phenolic compounds of claim 1, wherein the heteropolyacid catalyst has 30% loading.

10. The process for the selective alkylation of phenols or substituted phenolic compounds of claim 1, wherein the heating is carried out at 80° C. and for 6 hours.

11. The process for the selective alkylation of phenols or substituted phenolic compounds of claim 1, wherein the substrate is a cresol substrate.

* * * * *